United States Patent [19]
Creijghton

[11] Patent Number: 5,766,447
[45] Date of Patent: Jun. 16, 1998

[54] METHOD AND DEVICE FOR TREATING AN AQUEOUS SOLUTION

[75] Inventor: Yves L. M. Creijghton, Eindhoven, Netherlands

[73] Assignee: U.S. Philips Corporation, New York, N.Y.

[21] Appl. No.: 768,475

[22] Filed: Dec. 18, 1996

[30] Foreign Application Priority Data

Dec. 21, 1995 [EP] European Pat. Off. ............ 95203587

[51] Int. Cl.[6] ............................ C01B 13/11; C02F 1/46
[52] U.S. Cl. ............................ 205/742; 204/164; 204/165; 204/176; 422/186.07; 422/186.16; 422/907
[58] Field of Search ............................ 204/164, 165, 204/176; 422/186.07, 186.16, 907; 205/742

[56] References Cited

U.S. PATENT DOCUMENTS

| | | | |
|---|---|---|---|
| 4,051,043 | 9/1977 | Harter et al. | 250/531 |
| 5,464,513 | 11/1995 | Goriachev et al. | 204/164 |
| 5,478,533 | 12/1995 | Inculet | 422/186.07 |
| 5,549,795 | 8/1996 | Gregoire et al. | 204/164 |
| 5,630,915 | 5/1997 | Greene et al. | 204/164 |

OTHER PUBLICATIONS

A.K. Sharma et al, "A Preliminary Study of Pulsed Streamer Corona Discharge for the Degradation of Phenol in Aqueous Solutions", Hazardous Waste & Hazardous Materials 10 (2), 1993, pp. 209–219.

*Primary Examiner*—Arun S. Phasge
*Attorney, Agent, or Firm*—Anne E. Barschall

[57] ABSTRACT

The invention relates to a method and a device for treating an aqueous solution, in which a pulsed electric field is generated in the aqueous solution between two electrodes. In accordance with the invention, at least one of the electrodes is covered with a layer of a dielectric material which, during operation of the device, completely separates this (these) electrode(s) from the aqueous solution. This measure in accordance with the invention enables field strengths to be used which are much higher than those permissible in the known devices. The use of an oxygen-containing gas and a bipolarly pulsed electric field leads to a further improvement of the method in accordance with the invention.

16 Claims, 9 Drawing Sheets

METHOD AND DEVICE FOR TREATING AN AQUEOUS SOLUTION

The invention relates to a method of treating an aqueous solution, in which a pulsed electric field is generated in the aqueous solution between two electrodes. The invention further relates to a device for carrying out this method. Such a method and such a device can be used to purify or disinfect the aqueous solution used or to prepare or convert specific chemical compounds in said aqueous solution.

A method and a device of the type mentioned in the opening paragraph are known per se from the literature, such as Hazardous Waste & Hazardous Materials 10 (2), 1993, pp. 209–219. Such a device is shown, more particularly, in FIG. 2 of this publication. This device comprises a reactor chamber which accommodates a hollow, needle-shaped electrode as well as a circular second electrode which is situated at a distance of 50 mm from the needle tip.

The known method is carried out in this device by applying a pulsed electric field between the electrodes. In the experiments described, peak voltages of 25–40 kV, pulse durations of 500–1,000 ns, a pulse rise time of 20–50 ns and a frequency of 60 Hz are used. Under these conditions, very high electric fields, for example, of 100 kV/cm are formed at the needle-shaped electrode, so that the formation of so-called "streamer" discharges can take place. These discharges are characterized by the presence of filamentary discharge structures which are formed proximate to the tip of the needle-shaped electrode and extend in the direction of the other electrode.

Said known device and method enable phenol to be broken down in an aqueous solution under the influence of said pulsed electric field. In this process, collisions between electrons and water, and between electrons and substances dissolved in water or gaseous substances, such as oxygen, cause chemical reactive dissociation fragments to be formed, such as electrons, ions and radicals, for example hydroxyl radicals, atomic oxygen and atomic hydrogen. These dissociation products can either react directly, or via one or more intermediate products such as $HO_2$, $H_2O_2$ and $O_2^-$, with phenol in the aqueous solution and break it down.

The known method has an optimum effect if the electric field strength used is as high as possible. By increasing the average electric field strength, electrons in streamer discharges acquire a higher average energy. As a result, the energy consumption per chemically reactive dissociation product formed decreases, so that the efficiency of the purification process is increased. In addition, the direct killing effect of a pulsed electric field on micro-organisms is enhanced as the electric field strength is increased.

The known device has an important disadvantage. It has been found that the electric field strength of this device cannot be optimally adjusted. Above a specific average field strength, so-called "arc" discharges occur. These discharges are characterized by discharge channels having a high current density at a low voltage between the electrodes. The average energy of electrons in arc discharges is considerably lower than in streamer discharges, so that these electrons are used less efficiently to form chemically reactive dissociation fragments. The average density of electrons in arc discharges is considerably higher than in streamer discharges, so that arc discharges carry a much larger current. Consequently, the occurrence of arc discharges very adversely affects the efficiency with which chemically reactive dissociation fragments are formed. If use is made of the known device, such arc discharges can be precluded by choosing the average electric field strength to be smaller than 8 kV/cm.

In principle, the occurrence of arc discharges in the known method can be precluded by setting a maximum permissible voltage at which arc discharges are just not formed. However, in practice this measure is very difficult to carry out because said maximum permissible voltage depends on a large number of variable factors, such as (a) irregularities at the surface of the electrodes, (b) the shape of the voltage pulse and (c) the properties of the medium which is being treated, such as the conductivity and the percentage of gaseous substance.

In the case of an increase of the average electric field strength, the formation of arc discharges can alternatively be precluded, in principle, by limiting the voltage pulse duration. However, as the average electric field strength is increased, ever shorter voltage pulse durations are necessary to preclude arc discharges. The production of high-voltage pulses having a very high power and a very short pulse duration, for example above 10 megawatt (MW) during less than 1 microsecond, imposes high requirements on the electronic elements of the pulsed electric power supply unit. From this it follows that the efficiency with which the aqueous solution is treated increases as the electric field strength increases, but the cost price of the purification device which enables the necessary, short voltage pulse duration to be achieved, increases substantially.

It is an object of the invention to obviate the above disadvantage. The invention more particularly aims at providing a method by means of which the formation of arc discharges in the aqueous solution to be purified can be precluded in a simple manner. A further object of the invention is to supply a device which enables an aqueous solution to be efficiently treated electrochemically by means of a pulsed electric field, and which device is also relatively cheap.

These and other objects are achieved by a method of the type mentioned in the opening paragraph, which is characterized in accordance with the invention in that at least one of the electrodes is covered with a layer of a dielectric material, which completely separates this (these) electrode (s) from the aqueous solution.

The use of a layer of a dielectric material on one of the electrodes or on both electrodes enables the known method to be carried out at a higher average electric field strength. This enables a more efficient manner of treating an aqueous solution to be achieved. The dielectric constant of the dielectric material should preferably be much higher than that of the aqueous solution. Good results are achieved with a dielectric constant of 100. Preferably, the dielectric constant is in excess of 250. Particularly oxidic materials, such as preferably materials on the basis of barium titanate, can very suitably be used as the dielectric layer.

The invention is based on the experimentally gained insight that streamer discharges, which have formed in the aqueous solutions, can propagate in the form of surface streamer discharges on the surface of the dielectric material of the electrode. A local net-charge concentration on the dielectric material causes the electric field strength to increase substantially in these locations. Consequently, the electric field strength in the residual streamer channels decreases, causing the streamer discharges to be quenched. Consequently, the presence of a dielectric material, which completely separates one of the electrodes from the aqueous solution, is very suitable to preclude the formation of arc discharges.

The streamer discharges are preferably formed in a very inhomogeneous electric field. Such a field is preferably formed in the vicinity of a corona electrode. Such an electrode is characterized by a surface which locally has a very small radius of curvature, such as in the case of a thin wire, a sharp edge or a pointed tip. Preferably, the corona electrode is covered with a layer of a dielectric material with the exception of those parts of the electrode surface where the radius of curvature is small enough for the formation of streamer discharges. The dielectric constant of the dielectric material should preferably be much lower than that of the aqueous solution. Good results have been obtained with a dielectric constant of 5. The electric field strength at which streamer-formation occurs is preferably at least 25 kV/cm. The average electric field preferably has such a strength that streamer discharges can bridge the gap between the corona electrode and the dielectric material which covers the second electrode. To achieve this goal, the average electric field strength is preferably at least 5 kV/cm. It has been found that, preferably, use is made of a corona electrode with a radius of curvature in the range from 0.01 to 5 mm, a distance between both electrodes of 1–100 mm and a voltage-pulse height of 1–100 k.

A preferred embodiment of the method is characterized in that an oxygen-containing gas is introduced into the aqueous solution. The oxygen-containing gas bubbles present in the aqueous solution are divided into relatively small gas bubbles under the influence of the pulsed electric field in the vicinity of the electrode(s). The small gas bubbles thus formed contain chemically reactive components, such as ozone. These reactive components are formed as a result of the streamer discharges. By virtue of the presence of these discharges, dissociation of molecules, such as oxygen, can take place in an efficient manner. Such reactive components of the gas bubbles are effectively dissolved in the aqueous solution, partly because of the small diameter of said gas bubbles. In the absence of such relatively small gas bubbles, the process of mixing the reactive gaseous components with the aqueous solution would be less efficient.

An interesting embodiment of the method in accordance with the invention is characterized in that a bipolarly pulsed electric field is used. The use of a bipolarly pulsed electric field enables the aqueous solution to be treated more efficiently as regards the energy consumption of the process. After the formation of streamer discharges in the aqueous solution and the formation of streamer-surface discharges on the layer of the dielectric material during a first high-voltage pulse, the formation of new streamer discharges requires the recovery of the high electric field strength in the reactor chamber. This recovery occurs, inter alia, because in residual streamer channels in the aqueous solution and on the layer of the dielectric material, ions recombine to form neutral particles or diffuse in the aqueous solution. Thus, preferably, the first high-voltage pulse is succeeded by a second high-voltage pulse of opposite polarity, before a substantial part of the charge deposited on the layer of the dielectric material is absorbed in the aqueous solution. In this case, the surface charge deposited on the dielectric layer during a specific voltage pulse makes a first contribution to the formation of the (oppositely directed) electric field caused by the subsequent voltage pulse.

The use of high-voltage pulses of alternating polarity has additional advantages. For example, an accumulation of ions near the electrode, which may lead to a local reduction of the electric field, is largely precluded. Also local differences in concentration between negative and positive ions in the aqueous solution are reduced, so that the recombination of positive and negative ions to form neutral particles is promoted. Due to the electric field, the presence of relatively large numbers of ions leads to ion transport in the reactor chamber. This transport does not make a significant contribution to the production of chemically reactive dissociation fragments. For this reason, ion transport has a very negative effect on the amount of energy used to form chemically reactive dissociation fragments. These disadvantages are avoided when high-voltage pulses of alternating polarity are used.

Another interesting embodiment of the method in accordance with the invention is characterized in that the duty cycle of the bipolarly pulsed electric field is smaller than 0.01. By means of this measure, ion transport in an aqueous solution and the adverse effects involved are further reduced. It is noted that the expression "duty cycle" is to be understood to mean the ratio of the voltage-pulse duration to the voltage-pulse period. For example, at a pulse duration of less than 10 µs and a repetition frequency of 1 kHz (pulse period of 10 ms), a duty cycle of the desired value is achieved.

The invention also relates to a device for treating an aqueous solution, which device comprises a reactor chamber which accommodates two electrodes as well as a voltage source for applying a pulsed electric field between the two electrodes. In accordance with the invention, this device is characterized in that at least one of the electrodes is covered with a layer of a dielectric material which, during operation of the device, completely separates this (these) electrode(s) from the aqueous solution. Preferably, the dielectric constant of the dielectric material is much higher than that of the aqueous solution. Good results are achieved with a dielectric constant of 100. Preferably, the dielectric constant exceeds 250. Particularly oxidic materials, such as preferably materials on the basis of barium titanate, proved to be very suitable for use as a dielectric layer.

A preferred embodiment of the device in accordance with the invention is characterized in that the reactor chamber is also provided with one or more apertures through which an oxygen-containing gas is introduced. If, during operation of the inventive device, an oxygen-containing gas is present in the reactor chamber, the efficiency with which the aqueous solution is treated is higher. Preferably, this (these) aperture(s) is (are) provided in one of the electrodes. During operation of the device, this measure enables the gas bubbles to be concentrated in the part of the reactor chamber where the streamer discharges originate. This has a favorable effect on the efficiency of the method in accordance with the invention.

Another interesting embodiment of the device is characterized in accordance with the invention in that one of the electrodes is constructed as a corona electrode which, for this purpose, is provided with at least one part having a radius of curvature ranging between 0.01 and 5 mm. Streamer discharges are preferably formed in the vicinity of such a corona electrode, which forms a very inhomogeneous electric field. In another, very interesting embodiment, the corona electrode is provided with a layer of a dielectric material, with the exception of the parts whose radii of curvature range between 0.01 and 5 mm.

Good results are also achieved with a device in accordance with the invention, which is characterized in that granular material having a high dielectric constant is introduced into the reactor chamber. Preferably, an oxidic material, for example in the form of small pellets is used for this purpose. Materials which can very suitably be used are based on (doped) barium titanate.

These and other aspects of the invention will be apparent from and elucidated with reference to the embodiments described hereinafter.

It is noted that the (parts of the) devices shown in the Figures are not drawn to scale.

Figure 1:
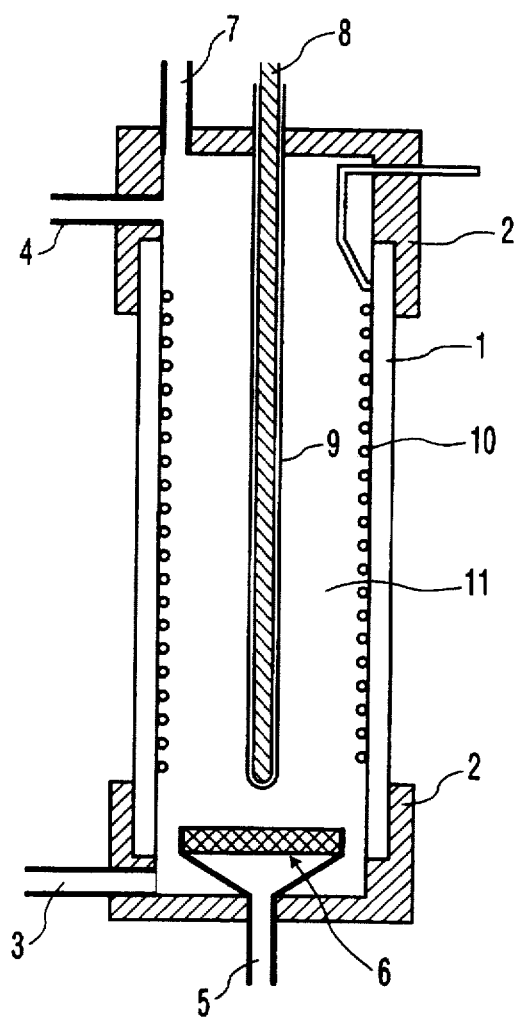
FIG. 1 is a schematic, cross-sectional view of a first embodiment of the device in accordance with the invention.

FIG. 1 is a schematic, cross-sectional view of a first embodiment of the device in accordance with the invention. This device comprises a reactor chamber (11), which is bounded by a cylindrical wall (1). In this case, said wall consists of a tube of a dielectric material, for example glass. The reactor chamber is closed at the upper and lower sides by electrically insulating parts (2), for example, of synthetic resin such as PTFE or PVDF. These synthetic resin parts are provided with apertures (3, 4) to supply and withdraw, respectively, the aqueous solution to be treated. During operation of the device, an oxygen-containing gas in the form of small gas bubbles can be introduced into the reactor chamber (11) via an aperture (5) and a diffusor (6). For the diffusor use can be made, for example, of a glass-filter plate. Any gas which is not dissolved in the aqueous solution during the treatment can be withdrawn via an aperture (7). The withdrawn gas, which may still contain chemically reactive components, can be supplied again to the aqueous solution, if desired.

A cylindrical electrode (8) is situated in the center of the tubular reactor chamber (11). This electrode is provided with a layer (9) of a dielectric material. As the entire surface of this electrode (8) is provided with layer (9), the electrode is entirely separated from the aqueous solution by this layer (9) during operation of the inventive device. The thickness of the layer (9) of a dielectric material is preferably small, for example 0.5–5 mm. Glass can be used as the dielectric material. Preferably, the layer (9) is made of a material whose dielectric constant is much higher than that of water, for example barium titanate ($BaTiO_3$). In this manner, the voltage across the dielectric, which is not used in the purification process, is limited.

A spiral-shaped corona electrode (10) which is made of a thin wire (thickness 0.4 mm) of, for example, stainless steel, adjoins the inner wall (1) of the reactor chamber (11). Parts of the surface of the corona electrode, where the electric field is relatively low, preferably adjoin a layer of a dielectric material whose dielectric constant is much lower than the dielectric constant of water. This method enables a higher electric field intensity in the aqueous solution to be attained by means of the corona electrode. Said electrode may be on the wall (11) or it may be partly incorporated therein. The minimum radius of curvature of the corona electrode is 0.1–1 mm. The distance between the turns of the spiral-shaped corona electrode is 1–50 mm and the distance from the corona electrode to the layer (9) of the dielectric material covering the central electrode is 1–100 mm.

The device can be operated with or without an injected, oxygen-containing gas. If the device is used in processes in which chemical reduction with free electrons and atomic hydrogen is desired, preferably, injected oxygen is dispensed with. In the presence of oxygen, $O_2^-$ radicals and $HO_2$ molecules, which contribute to chemical oxidation, are formed from free electrons and atomic hydrogen.

The reactor chamber (11) of the device in accordance with the invention is preferably filled with a granular material (not shown), which is, for example, in the form of pellets. These pellets are solid grains between which the aqueous solution and the oxygen-containing gas can flow. The pellets are preferably made of a dielectric material having a high dielectric constant, for example barium titanate. As a result of electric surface-discharges on the pellets or electric discharges between electrically polarized pellets, the presence of such pellets may increase the efficiency with which chemically reactive dissociation fragments are formed in the aqueous solution. To achieve a further increase of the efficiency with which the aqueous solution is treated, the pellets may be provided with a catalytic material which influences the chemical kinetics.

Figure 2A:
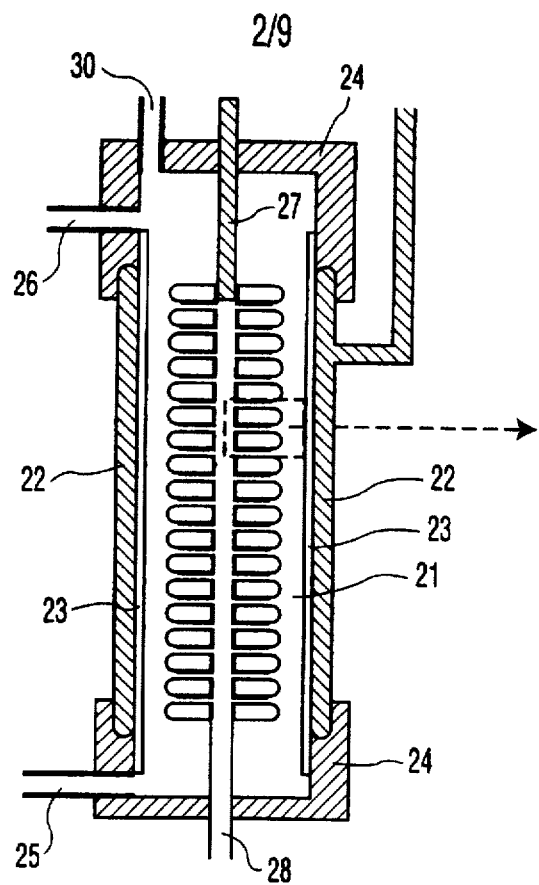
FIGS. 2(a and b) are schematic, cross-sectional views of a second embodiment of the device in accordance with the invention.
Figure 2B:
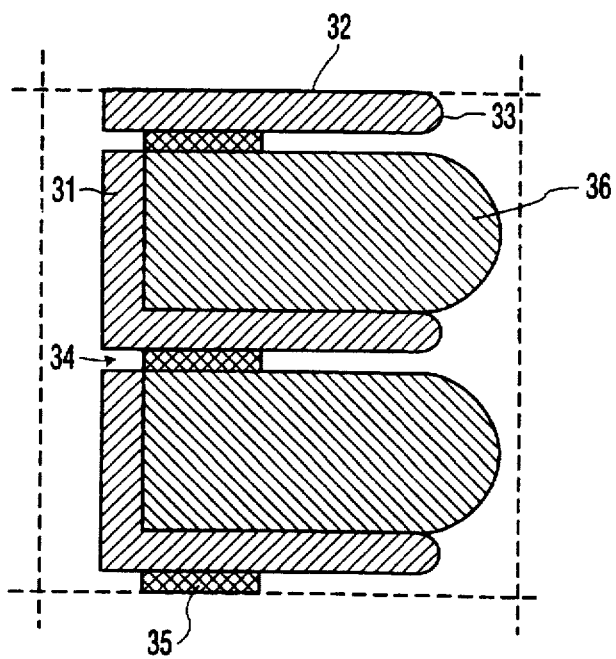

FIG. 2 is a schematic, cross-sectional view of a second embodiment of the device in accordance with the invention. The reactor chamber (21) shown in FIG. 2-a comprises a cylindrical, external electrode (22) whose inner surface is covered with a layer of a dielectric material (23). During operation of the device, this material (23) completely separates the external electrode (22) from the aqueous solution to be treated in the reactor chamber. Preferably, the dielectric material (23) has a high dielectric constant and a small thickness. Said dielectric material consists, for example, of a layer of barium titanate having a thickness of 1–5 mm. The reactor chamber is closed at the upper and lower sides by electrically insulating parts (24) of synthetic resin, for example PTFE or PVDF. These parts are provided with apertures (25, 26) to supply and withdraw, respectively, the aqueous solution to be treated.

A corona electrode (27) is centrally arranged in the reactor chamber (21). During operation of the inventive device, an oxygen-containing gas can be introduced into the reactor chamber via the inlet aperture (28) of an electrically insulating synthetic resin tube (29) and apertures in the corona electrode (27). Any gas which is not dissolved in the aqueous solution is withdrawn via the outlet aperture (30). The withdrawn gas, which may still contain chemically reactive components, can be supplied to the aqueous solution again, if desired.

A part of the corona electrode (27) is shown in greater detail in FIG. 2-b. The corona electrode is built up of a central, tubular conductor (31) of metal (for example stainless steel), to which thin, circular discs (32) are connected in an electrically conducting manner. The thickness of the discs ranges from 0.2 to 10 mm. Said discs have a more or less sharp edge (33) whose radius of curvature ranges from approximately 0.01 to 5 mm. Via apertures (34) in the central tubular conductor (10), an oxygen-containing gas can be passed through a diffusor (35) to the sharp edges (33) of the discs. The diffusor may consist of a porous ceramic material, for example glass filter. A layer (36) of a dielectric material, which preferably has a low dielectric constant, adjoins the top side of the discs. The presence of this dielectric material causes the electric field strength and the inhomogeneity of the field at the sharp edges (33) of the corona electrode to be increased. Relatively small gas bubbles and chemically reactive dissociation fragments in gas bubbles form at the sharp edges (33) of the corona electrode.

Although the temperature in streamer discharges is much lower than in arc discharges, high temperatures may also locally occur in streamer discharges, for example at the corona electrode. For this reason, the dielectric material between the discs is preferably resistant to a high temperature and is chemically inert. Consequently, said material is preferably made of a synthetic resin. Good results have been achieved with PTFE and PVDF.

Figure 3:
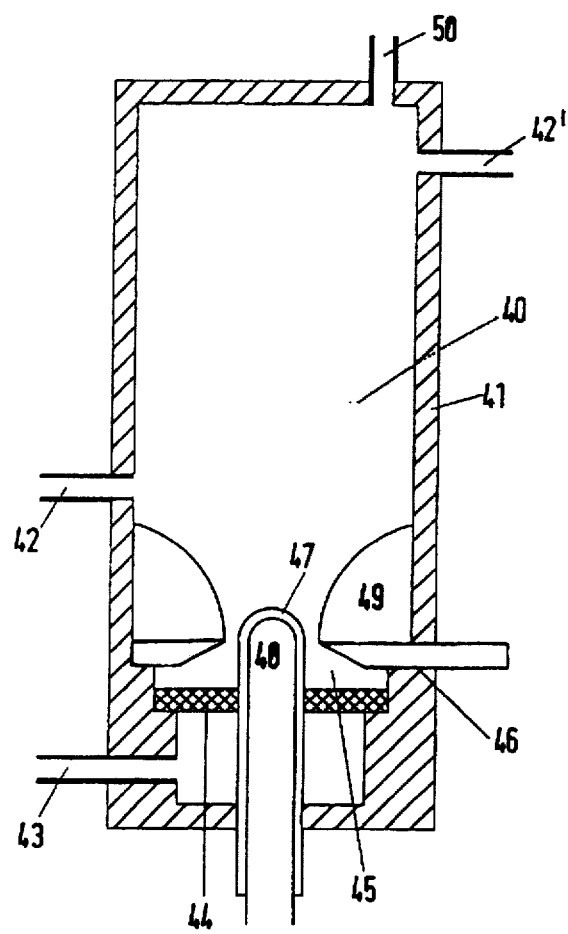
FIG. 3 is a schematic, cross-sectional view of a third embodiment of the device in accordance with the invention.

FIG. 3 shows a schematic, cross-sectional view of a third inventive device for treating aqueous solutions. This device comprises a reactor chamber (40) which is also bounded by a wall (41). This wall (41) is tubular and built up of an electrically insulating material, for example glass. In wall (41) there are apertures (42 and 42') for supplying and withdrawing, respectively, an aqueous solution to be treated. During operation of the device, an oxygen-containing gas can be passed along a supply pipe (43), via a porous ceramic material (44) (for example a glass filter), to a space (45) in which a substantial part of the oxygen-containing gas is collected. At the upper side of this cavity there is an aperture which is bounded, on the one hand, by a corona electrode (46) provided with a circular, sharp edge, and, on the other hand, by a layer (47) of a dielectric material which entirely covers a second cylindrical electrode (48). The dielectric material preferably has a dielectric constant which is much higher than that of water. For the dielectric material use can be made, in particular, of ceramic materials, such as, preferably, ceramic materials based on (doped) barium titanate. The top side of the corona electrode is covered with a dielectric material (49) having, preferably, a relatively low dielectric constant, such as glass or PTFE.

The porous ceramic material (44) serves first of all to preclude the inflow of water into the gas pipe (43) when the gas pressure is absent or low. This may be the case when, during operation of the device, no or little oxygen-containing gas is introduced into the aqueous solution. To improve the sealing function of the glass filter, the material (44) is preferably provided with a hydrophobic material. When the space (45) is filled with an aqueous solution, said aqueous solution is removed from this cavity by means of gas pressure. The gas flows through the aperture which is bounded by both electrodes. The gas bubbles and the streamer discharges are properly mixed by the pulsed electric field.

A second function of the porous ceramic material (44) concerns the mixture of the aqueous solution and the oxygen-containing gas. By virtue of the spatially uniform inflow of gas into the water, an efficient mixture is obtained. As a result thereof, the inhomogeneous electric field generated by the corona electrode (46) does not differ very much from the field obtained in the aqueous solution without gas bubbles. By applying a bipolarly pulsed high voltage between the electrodes (6) and (8), small gas bubbles containing chemically reactive components, inter alia ozone, are formed in the aqueous solution. Any gases which are not dissolved in the aqueous solution are withdrawn via the outlet aperture (50). The withdrawn gas, which may still contain chemically reactive components, can be added to the aqueous solution again, if desired. The radius of curvature at the edge of the corona electrode is 0.01–5 mm and the distance from this edge to the dielectric (7) is 0.1–5 mm.

Figure 4A:
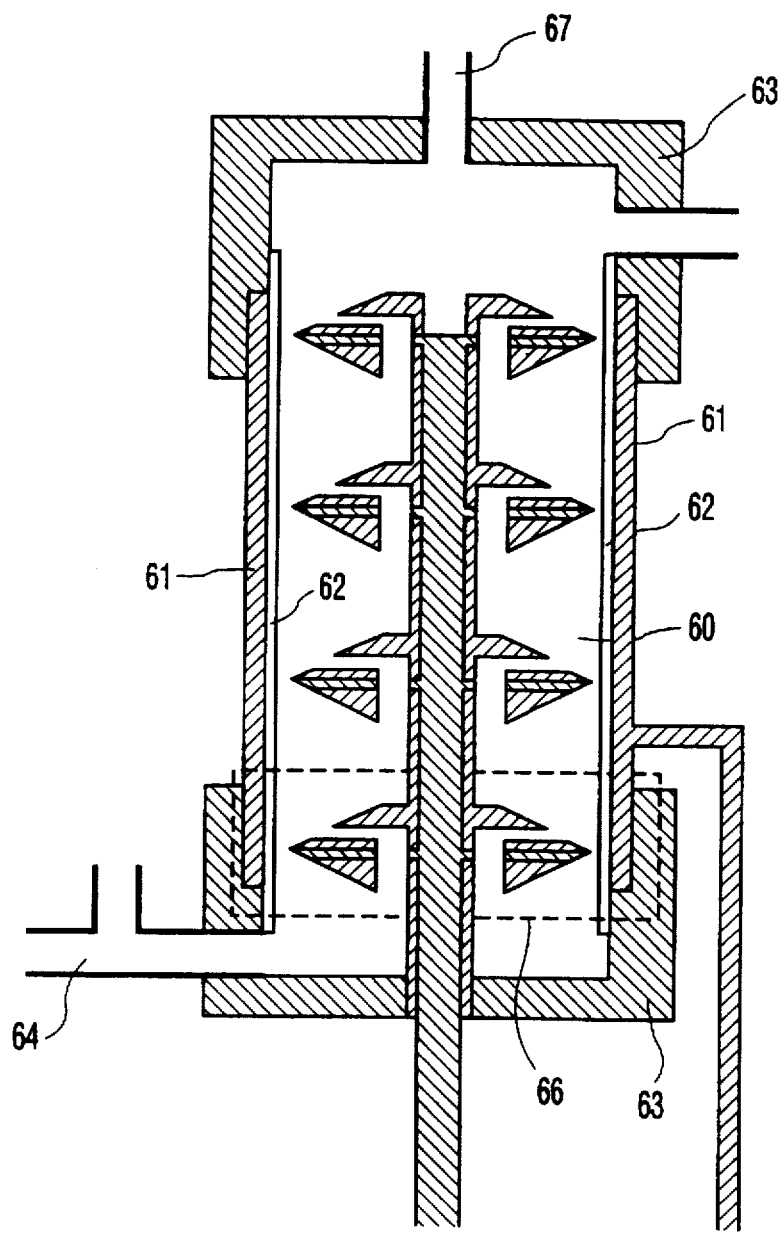
FIGS. 4(a and b) are schematic, cross-sectional views of a fourth embodiment of the device in accordance with the invention.
Figure 4B:
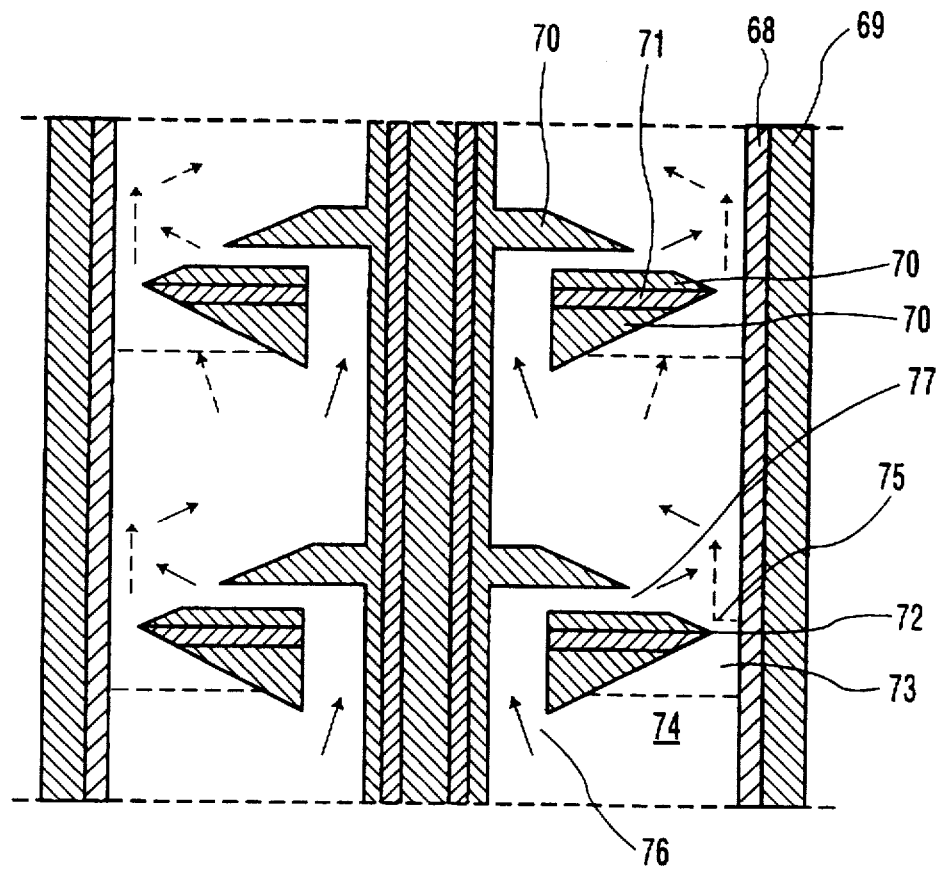

FIG. 4-a is a schematic, cross-sectional view of a fourth device in accordance with the invention. In this embodiment, the reactor chamber (60) is bounded by a tubular external electrode (61) whose inner surface is covered with a layer (62) of a dielectric material. During operation of the device, this material completely separates the external electrode from the aqueous solution to be treated, which is present in the reactor chamber. The dielectric material of layer (62) preferably has a high dielectric constant and a small thickness. It is preferably made of a ceramic material, such as barium titanate, and has a layer thickness, for example, of 1–5 mm.

The reactor chamber is closed at the upper and lower sides by electrically insulating parts (63) which are made of a synthetic resin, for example PTFE or PVDF. These parts are provided with apertures (64) and (65) for supplying and withdrawing, respectively, the aqueous solution to be treated. The water supplied entrains, preferably, an oxygen-containing gas. In the reactor chamber there are one or more elements (66) for forming small gas bubbles having chemically reactive substances in the aqueous solution, which gas bubbles will be described in greater detail in FIG. 4-b. The electrically insulating closure at the upper side of the device is provided with an aperture (67) for the withdrawal of gas which is not dissolved in the aqueous solution. The gas withdrawn, which may still contain chemically reactive components, may be supplied again to the aqueous solution, if desired.

FIG. 4-b is a schematic cross-sectional view of an element (66) which is used to form small gas bubbles with chemically reactive substances in the aqueous solution, said Figure also shows the surrounding dielectric (68) and the surrounding tubular electrode (69). Such an element comprises a dielectric material (70) having a low dielectric constant, for example glass or PTFE, as well as a flat circular electrode (71) having a sharp edge (72). The dielectric material and the dielectric wall of the reactor chamber (68) together form a space (73) which is characterized by a relatively large aperture (74) at the lower side and a relatively small aperture (75) at the upper side. If sufficient oxygen-containing gas is supplied to the aqueous solution, oxygen-containing gas will be permanently collected in the space (74) during operation of the device.

The use of a (preferably: bipolarly) pulsed electric field between the electrodes (69) and (71) in the vicinity of the outlet aperture for gas (75), causes small gas bubbles with chemically reactive substances to be formed in the aqueous solution. To enable the aqueous solution to flow through the device, each element comprises channels having inlet apertures at the lower side (76) and outlet apertures at the upper side (77). The outlet apertures for the aqueous solution are preferably situated proximate to the outlet aperture for gas (75). The radius of curvature at the edge of the corona electrode (72) is 0.01–5 mm and the distance from this edge to the dielectric (68) is 0.1–5 mm.

Figure 5A:
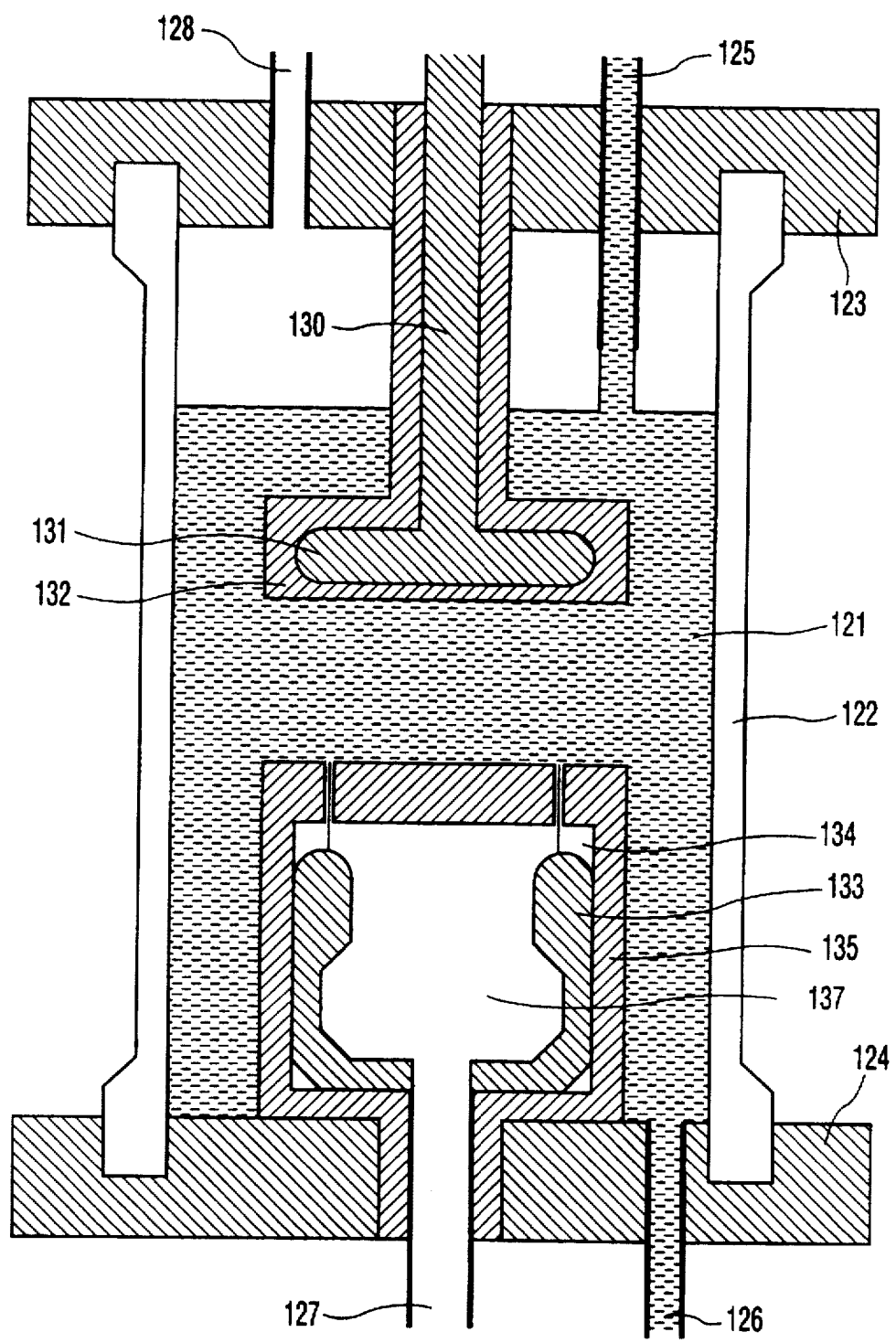
FIGS. 5(a and b) are schematic, cross-sectional views of a fifth embodiment of the device in accordance with the invention.
Figure 5B:
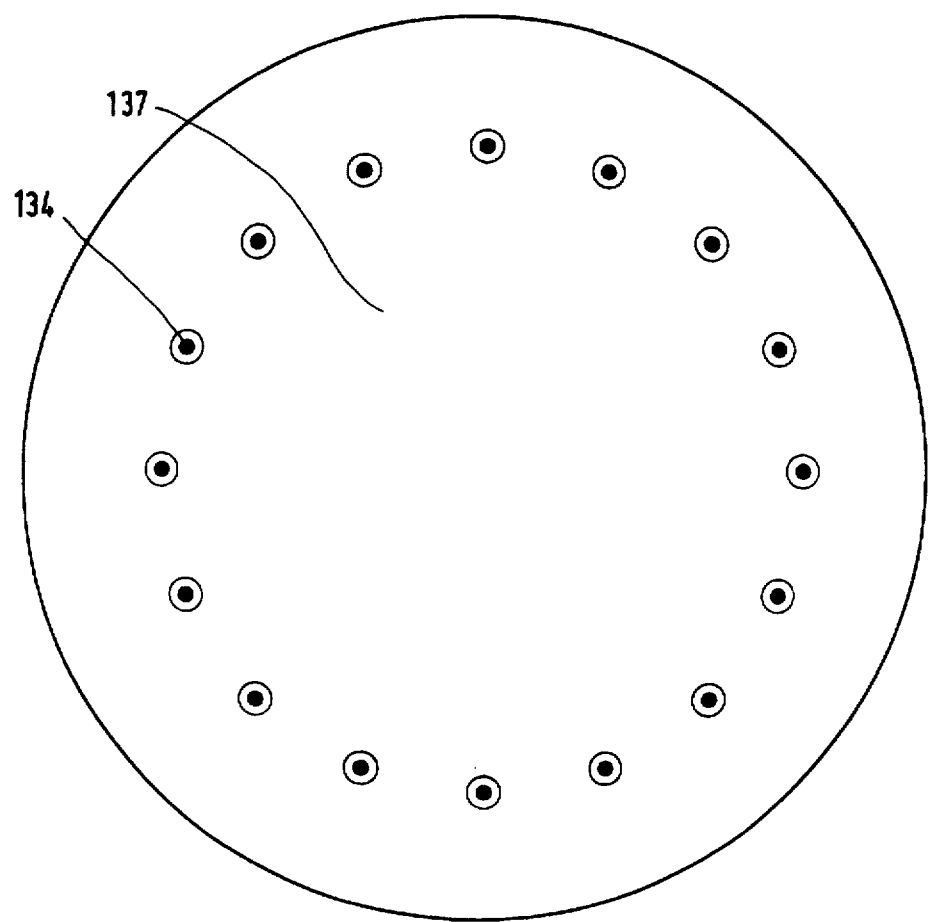

FIG. 5-a shows a schematic, cross-sectional view of a fifth embodiment of the device in accordance with the invention. This device comprises a reactor chamber (121) which is bounded by an electrical insulating cylindrical wall (122). In this case, said wall consists of glass. The reactor chamber is closed at the upper and lower sides by electrically insulating parts (123, 124), for example, of a synthetic resin such as PTFE or PVDF. These synthetic resin parts are provided with apertures (125, 126) to supply and withdraw, respectively, the aqueous solution to be treated.

An oxygen containing gas can be supplied to the aqueous solution via the aperture (127) of the corona-electrode (133). Any gas which is not dissolved in the aqueous solution is withdrawn via the outlet aperture (128). The withdrawn gas, which may still contain chemically reactive components, can be supplied to the aqueous solution again, if desired via aperture (127) of the corona-electrode.

A grounded electrode is centrally arranged in the reactor chamber (121). This electrode is built up of a central, tubular conductor (130) and a circular disk (131). The radius of curvature at the edge of the disk is preferentially larger than 5 mm. The grounded electrode is made of metal, for example steel. The grounded electrode (130, 131) is covered by a dielectric layer (132) which entirely separates said electrode from the aqueous solution. Preferably, the dielectric layer (132) has a high dielectric constant and a small thickness. Said dielectric layer consists, for example, of a layer of (doped) barium titanate having a thickness of 1–5 mm. Also with a glass layer having a thickness of 2 mm good results have been obtained.

A corona-electrode (133) is centrally arranged in the reactor chamber (121). The corona electrode is built up of a conductor of metal (for example stainless steel) to which thin needles (134) are connected in an electrically conducting manner. The radius of curvature of the needles ranges from 0.2 to 4 mm. The corona-electrode is surrounded by a dielectric material (135), with the exception of the tips (136) of the needles. Said dielectric material (135) adjoins the tips of the needles and preferably has a low dielectric constant. During operation of the inventive device, an oxygen-containing gas can be introduced in the corona-electrode (133) via the inlet aperture (127). In the corona-electrode a space (137) exists for distribution of the oxygen-containing gas along the different needles.

FIG. 5-b is a cross-sectional view of the corona-electrode showing a circular arrangement of needles (138) in the dielectric material (139). The distance between the needles is preferentially in the range 4–20 mm.

The device of FIG. 5 was used to demonstrate an improved conversion efficiency. Said device contained 16 needles (124) of steel with a tip radius of 0.1 mm and a needle diameter of 0.8 mm. The diameter of the tubular holes surrounding said needles was 1.0 mm. A glass layer of 2 mm thickness was used as a dielectric layer (132). The electrode distance, i.e. the distance between the grounded electrode and the tips of the needles, was variable between 4 and 10 mm.

Experiments were carried out with this device using alternative positive and negative pulses with a regular time interval of 10 ms between pulses of opposite polarity. The peak voltages were –48 kV and +48 kV. The pulse duration (width at half maximum) was 2 microseconds.

In a first experiment, a solution of 30 mg Acid Blue 40 dissolved in 1 l tap water was treated by means of the inventive method in the device as described above. Pure oxygen was added in the solution. When using an electrode distance of 10 mm, an average field strength of 4 kV/mm was reached. No spark formation was observed, irrespective whether dielectric layer (132) was present or not on the ground electrode. After 20 minutes of operation, (60 Watt, 72 kJ), about 50% of the Acid Blue 40 was converted. The energy efficiency was determined to be 0.21 mg/kJ.

In a second experiment, the same solution was treated under the same conditions, using now a distance of 5 mm between the electrodes. In this situation, the average field strength is about 8 kV/mm. Without the layer (132) of dielectric material, the device could not operate without spark formation. Using said layer (132) as described above, after 12 minutes of operation (60 Watt, 43.2 kJ), about 50% of the Acid Blue 40 was converted. The energy efficiency was determined to be 0.35 mg/kJ.

These experiments show that an increase of the average field strength results in an increase of the energy efficiency of the conversion process. They show moreover that the use of a dielectric layer is necessary in order to operate the device under optimum voltage conditions avoiding the formation of sparks.

Figure 6A:
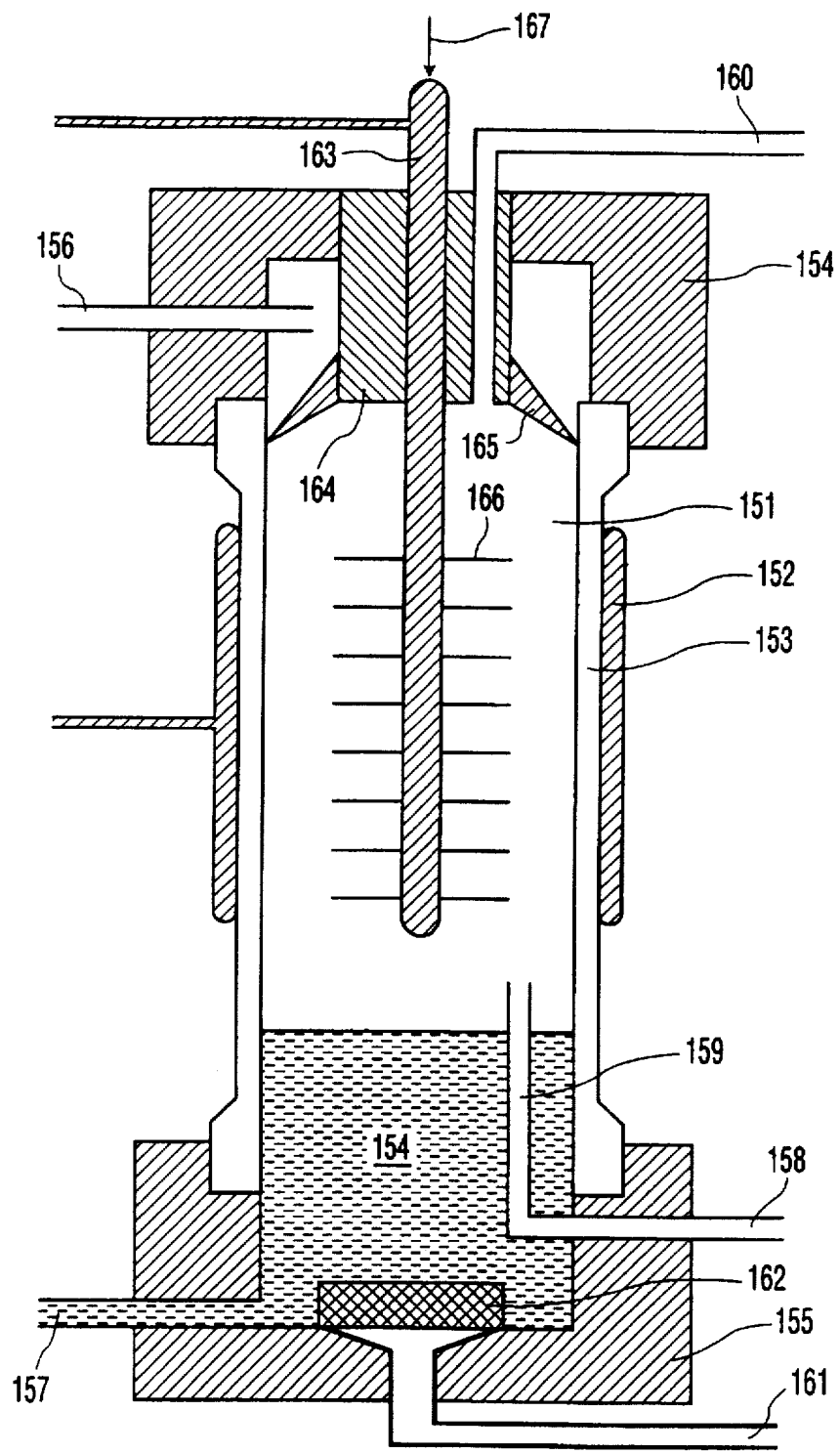
FIGS. 6(a and b) are schematic, cross-sectional views of a sixth embodiment of the device in accordance with the invention.
Figure 6B:
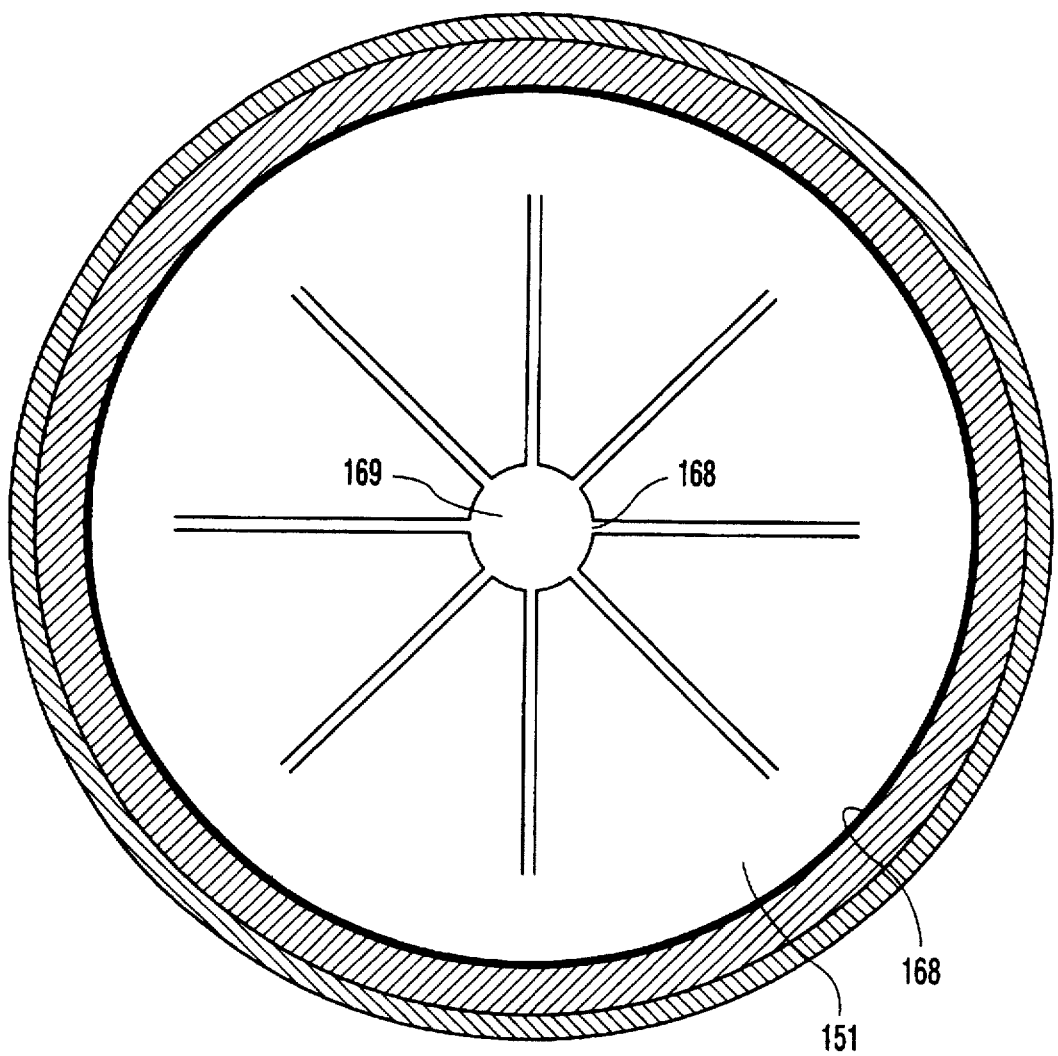

FIG. 6-a is a schematic, cross-sectional view of a sixth embodiment of the device in accordance with the invention which is most preferred because of its simple construction. The reactor chamber (151) comprises a cylindrical, external electrode (152) whose inner surface is covered with a layer of dielectric material (153). The reactor chamber is closed at the upper and lower sides by electrically insulating parts (154, 155). These parts are provided with apertures (156, 157) to supply and withdraw, respectively, the aqueous solution to be treated. During operation of the device a film of aqueous solution is flowing, along the inner surface of the dielectric material (153) from the top of the reactor to the bottom of the reactor where it is collected in a part (154) of the reactor chamber (151). Said dielectric material (153) completely separates the external electrode (152) from the aqueous solution to be treated in the reactor chamber. Preferably, the dielectric material (153) has a high dielectric constant and a small thickness. Said dielectric material consists, for example, of a layer of barium titanate having a thickness of 1–5 mm.

An aperture (158) is provided in the bottom-end (155) of the reactor to supply an oxygen-containing gas. The oxygen-containing gas is fed via the insulating tube (159) to the part of the reaction chamber (151) which is above the level of the aqueous solution. Any gas which is not dissolved in the aqueous solution is withdrawn via the outlet aperture (160) in the top-end (154) of the reactor. The withdrawn gas, which still may contain chemically reactive components such as ozone, can be supplied to the aqueous solution again, if desired, via the inlet aperture (161) in the bottom-end (15) of the reactor. Said gas is distributed in the aqueous solution in the form of small bubbles produced with diffusor (162). For the diffuser use can be made, for example, of a glass-filter plate.

A high voltage conductor (163) is introduced into the reactor chamber via the electrically insulating feed-through (164). A ring-shaped, electrically insulated part (165) is connected to the feed-through (164). This ring (165) has two different functions.

A first function of the ring (165) is to distribute in a uniform manner the aqueous solution, entering the reaction chamber (161) through the aperture (156), along the dielectric layer (153) covering the external electrode (152). In this manner a film of aqueous solution, flowing from the top to the bottom of the reactor, is formed. A second function of the ring (165) is to collect any gas which is not dissolved in the aqueous solution and which can be withdrawn via the outlet aperture (160).

A corona-electrode is centrally arranged in the reaction chamber (151). The corona-electrode is built-up of a central, tubular conductor (163) to which a number of conductors (166) with sharp edges or tips are connected in an electrically conducting manner. The sharply curved conductors (166) may consist of needles or thin disks. Said needles preferentially have a tip radius of curvature ranging from 0.1 to 1 mm. Said disks preferentially have a more or less sharp edge whose radius of curvature ranges from 0.01 to 1 mm. The distance between the sharply curved conductors (164)

and the film of aqueous solution, flowing along the dielectric (153), is preferably in the range 1–10 mm.

An inventive mode of operation of the device uses the injection of an oxygen-containing gas into the reaction chamber via the inlet aperture (167) of the corona-electrode and via apertures in the sharply curved conductors (166). When the reactor is operated with an oxygen-containing gas supplied via the corona-electrode, the supply of an oxygen-containing gas via the aperture (158) can be avoided.

A cross-sectional view of the corona-electrode is shown in FIG. 6-b. An oxygen-containing gas can flow via holes (168) in the tubular electrode (167), via hollow needles (166) to the reaction chamber (151). The outer radius of the hollow needles is preferentially in the range 0.4–2 mm, the inner radius is preferentially in the range 0.1–1 mm. During operation of the inventive device streamer discharges are observed in the oxygen-containing gas and adjoin the film of aqueous solution (168).

The device of FIG. 6 was used to demonstrate an improved conversion efficiency. Said device contained a 2 mm thick layer of dielectric material (glass). The needles had a radius of 1 mm and a tip radius of curvature of 0.1 mm. The distance between the tip of the needles and the aqueous film was 10 mm.

Experiments were carried out with this device using alternative positive and negative pulses with a regular time interval of 20 ms between pulses of opposite polarity. The peak voltages were −45 kV and +45 kV. The pulse duration (width at half maximum) was 2 microseconds.

In a first experiment, a solution of 20 mg Acid Blue 40 dissolved in 1 l tap water was treated by means of the inventive method in the device as described above. Pure oxygen was added in the solution. After 20 minutes of operation, (60 Watt, 72 kJ), about 98% of the Acid Blue 40 was converted. The energy efficiency was determined to be 1.0 mg/kJ.

In a second experiment, a solution of 100 mg Acid Blue 40 dissolved in 0.8 l tap water was treated under the same conditions. After 5 minutes of operation (60 Watt, 16 kJ), about 47% of the Acid Blue 40 was converted. The energy efficiency was determined to be 2.0 mg/kJ.

In a third experiment, a solution of 40 mg phenol dissolved in 0.8 l tap water was treated under the same conditions. After 30 minutes of operation (60 Watt, 144 kJ), about 85% of the phenol was converted. The energy efficiency was determined to be 0.24 mg/kJ.

The method and the device described hereinabove enable an aqueous solution to be treated efficiently by means of a pulsed electric field. The presence of a layer of a dielectric material on at least one of the electrodes of the device permits field strengths to be used which are much higher than the field strengths permissible in the known devices. The use of an oxygen-containing gas and a bipolarly pulsed electric field leads to a further improvement of the method in accordance with the invention.

I claim:

1. A method of treating an aqueous solution, in which a pulsed electric field is generated in the aqueous solution between two electrodes, characterized in that at least one of the electrodes is covered with a layer of a dielectric material, which completely separates this (these) electrode(s) from the aqueous solution.

2. A method as claimed in claim 1, characterized in that an oxygen-containing gas is introduced into the aqueous solution.

3. A method as claimed in claim 1, characterized in that a bipolarly pulsed electric field is used.

4. A method as claimed in claim 1, characterized in that the duty cycle of the pulsed electric field is smaller than 0.01.

5. The device of claim 1 wherein the pulse duration is approximately one to two microseconds.

6. The device of claim 1 wherein the dielectric is at least partly in physical contact with the aqueous solution.

7. A device for treating an aqueous solution, which device comprises a reactor chamber which accommodates two electrodes as well as a voltage source for applying a pulsed electric field between the two electrodes, characterized in that at least one of the electrodes is covered with a layer of a dielectric material which, during operation of the device, completely separates this (these) electrode(s) from the aqueous solution.

8. A device as claimed in claim 7, characterized in that the reactor chamber is also provided with one or more apertures through which an oxygen-containing gas is introduced.

9. A device as claimed in claim 8, characterized in that the aperture(s) is (are) provided in one of the electrodes.

10. A device as claimed in claim 7, characterized in that one of the electrodes is constructed as a corona electrode which, for this purpose, is provided with at least one part having a radius of curvature ranging between 0.01 and 5 mm.

11. A device as claimed in claim 10, characterized in that the corona electrode is provided with a layer of a dielectric material, with the exception of the parts whose radii of curvature range between 0.01 and 5 mm.

12. A device as claimed claim 7, characterized in that a granular material having a high dielectric constant is introduced into the reactor chamber.

13. A device for treating an aqueous solution, the device comprising first and second electrodes, the first electrode being substantially immersed in the aqueous solution, the second electrode having a dielectric disposed in contact with the second electrode and in contact with the aqueous solution, the first and second electrodes functioning to create a pulsed electric field in the aqueous solution.

14. The device of claim 13 wherein the first electrode comprises at least one corona needle tip; and the first and second electrode function to create a streamer discharge through the aqueous solution from the needle tip to the second electrode.

15. The device of claim 14 wherein the first and second electrodes are such that, in operation without the dielectric, arc discharges would form in the aqueous solution; but, in operation with the dielectric, such arc discharges are reduced with respect to the operation without the dielectric.

16. The device of claim 14 wherein the streamer discharge functions to kill microorganisms in the aqueous solution by direct electrical effect.

* * * * *